United States Patent
Adams et al.

(10) Patent No.: US 8,801,749 B2
(45) Date of Patent: Aug. 12, 2014

(54) RAPID EXCHANGE CATHETERS USABLE WITH EMBOLIC PROTECTION DEVICES

(75) Inventors: Daniel O. Adams, Long Lake, MN (US); Marwane S. Berrada, Montreal (CA); Cathleen M. von Lehe, Rogers, MN (US); Richard S. Kusleika, Eden Prairie, MN (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/223,774

(22) Filed: Sep. 1, 2011

(65) Prior Publication Data

US 2012/0053615 A1    Mar. 1, 2012

Related U.S. Application Data

(63) Continuation of application No. 12/100,837, filed on Apr. 10, 2008, now abandoned, which is a continuation of application No. 12/021,008, filed on Jan. 28, 2008, now abandoned, which is a continuation of application No. 10/171,704, filed on Jun. 14, 2002, now Pat. No. 7,717,934.

(51) Int. Cl.
*A61M 29/00* (2006.01)
*A61M 5/00* (2006.01)
*A61F 11/00* (2006.01)

(52) U.S. Cl.
USPC ...... 606/200; 606/108; 606/191; 604/103.04; 604/264

(58) Field of Classification Search
CPC .............. A61M 25/00; A61M 25/001; A61M 25/0012; A61M 25/0015
USPC ................ 606/113, 114, 127, 191–198, 200; 623/1.11, 1.35

See application file for complete search history.

(56) References Cited

U.S. PATENT DOCUMENTS

| | | | |
|---|---|---|---|
| 4,180,076 A | 12/1979 | Betancourt | |
| 4,552,554 A | 11/1985 | Gould et al. | |
| 4,704,111 A | 11/1987 | Moss | |
| 4,748,982 A | 6/1988 | Horzewski et al. | |
| 4,762,129 A | 8/1988 | Bonzel | |
| 4,921,479 A | 5/1990 | Grayzel | |

(Continued)

FOREIGN PATENT DOCUMENTS

| | | |
|---|---|---|
| EP | 0 592 720 A1 | 4/1994 |
| EP | 0 592 720 B1 | 4/1994 |

(Continued)

OTHER PUBLICATIONS

European Search Report EP 03 741 887.8 dated Jul. 25, 2013.

*Primary Examiner* — Tuan V Nguyen
(74) *Attorney, Agent, or Firm* — Alana T. Bergman, Esq.

(57) ABSTRACT

Catheters, assemblies, and methods for delivering and recovering embolic protection devices. Catheters are provided that can be advanced over single length guide wires and which can be retracted over single length wire shafts of distal embolic protection devices. One catheter is a two-port catheter having two sidewall ports, a distal end port, and a proximal end port. The two-port catheter can be advanced over a guide wire threaded between the distal end port and the distal sidewall port. An embolic protection device wire shaft can be back loaded into the distal end port and out the proximal sidewall port. A three-port catheter includes a distal end port, and distal, intermediate, and proximal sidewall ports.

5 Claims, 13 Drawing Sheets

(56) References Cited

U.S. PATENT DOCUMENTS

| | | | |
|---|---|---|---|
| 4,928,693 A | 5/1990 | Goodin et al. | |
| 4,932,413 A | 6/1990 | Shockey et al. | |
| 4,947,864 A | 8/1990 | Shockey et al. | |
| 4,988,356 A | 1/1991 | Crittenden et al. | |
| 5,135,535 A | 8/1992 | Kramer | |
| 5,195,978 A | 3/1993 | Schiffer | |
| 5,203,338 A | 4/1993 | Jang | |
| 5,205,822 A | 4/1993 | Johnson et al. | |
| 5,234,407 A | 8/1993 | Teirstein et al. | |
| 5,263,932 A | 11/1993 | Jang | |
| 5,290,232 A | 3/1994 | Johnson et al. | |
| 5,324,269 A | 6/1994 | Miraki | |
| 5,342,297 A | 8/1994 | Jang | |
| 5,342,371 A | 8/1994 | Welter et al. | |
| 5,389,087 A | 2/1995 | Miraki | |
| 5,415,639 A * | 5/1995 | VandenEinde et al. | 604/528 |
| 5,417,669 A | 5/1995 | Castaneda et al. | |
| 5,496,346 A | 3/1996 | Horzewski et al. | |
| 5,531,700 A | 7/1996 | Moore et al. | |
| 5,626,600 A | 5/1997 | Horzewski et al. | |
| 5,658,262 A | 8/1997 | Castaneda et al. | |
| 5,735,828 A | 4/1998 | Jungnelius | |
| 5,911,734 A | 6/1999 | Tsugita et al. | |
| 5,921,971 A * | 7/1999 | Agro et al. | 604/523 |
| 5,947,995 A | 9/1999 | Samuels | |
| 6,056,719 A | 5/2000 | Mickley | |
| 6,068,610 A | 5/2000 | Ellis et al. | |
| 6,099,497 A | 8/2000 | Adams et al. | |
| RE36,857 E | 9/2000 | Euteneuer et al. | |
| 6,142,987 A | 11/2000 | Tsugita | |
| 6,159,195 A | 12/2000 | Ha et al. | |
| 6,245,089 B1 | 6/2001 | Daniel et al. | |
| 6,248,092 B1 | 6/2001 | Miraki et al. | |
| 6,287,291 B1 | 9/2001 | Bigus et al. | |
| 6,371,971 B1 | 4/2002 | Tsugita et al. | |
| 6,387,119 B2 | 5/2002 | Wolf et al. | |
| 6,450,987 B1 | 9/2002 | Kramer | |
| 6,468,291 B2 | 10/2002 | Bates et al. | |
| 6,511,492 B1 | 1/2003 | Rosenbluth et al. | |
| 6,527,746 B1 | 3/2003 | Oslund et al. | |
| 6,530,939 B1 | 3/2003 | Hopkins et al. | |
| 6,537,294 B1 * | 3/2003 | Boyle et al. | 606/200 |
| 6,551,269 B2 | 4/2003 | Clemens et al. | |
| 6,613,013 B2 | 9/2003 | Haarala et al. | |
| 6,652,505 B1 | 11/2003 | Tsugita | |
| 6,752,813 B2 | 6/2004 | Goldfarb et al. | |
| 6,821,287 B1 * | 11/2004 | Jang | 606/194 |
| 7,169,165 B2 | 1/2007 | Belef et al. | |
| 7,717,934 B2 | 5/2010 | Kusleika | |
| 2001/0025186 A1 | 9/2001 | Kramer | |
| 2002/0022858 A1 | 2/2002 | Demond et al. | |
| 2002/0042626 A1 | 4/2002 | Hanson et al. | |
| 2002/0095141 A1 | 7/2002 | Belef et al. | |
| 2002/0177870 A1 | 11/2002 | Sepetka et al. | |
| 2003/0004537 A1 | 1/2003 | Boyle et al. | |
| 2003/0004541 A1 | 1/2003 | Linder et al. | |
| 2003/0032941 A1 | 2/2003 | Boyle et al. | |
| 2008/0119890 A1 | 5/2008 | Adams et al. | |
| 2008/0188888 A1 | 8/2008 | Adams et al. | |
| 2010/0179491 A1 | 7/2010 | Adams et al. | |

FOREIGN PATENT DOCUMENTS

| | | |
|---|---|---|
| EP | 0 807 448 A1 | 11/1997 |
| EP | 1177777 A3 | 2/2002 |
| EP | 1 351 737 B1 | 7/2005 |
| WO | WO 94/25096 A1 | 11/1994 |
| WO | WO 96/01591 A1 | 1/1996 |
| WO | WO 01/08743 A1 | 2/2001 |
| WO | WO 02/11627 A2 | 2/2002 |
| WO | WO02/028292 A1 | 4/2002 |
| WO | WO 02/062266 A2 | 8/2002 |
| WO | WO 02/069846 A2 | 9/2002 |
| WO | WO 03/009781 A1 | 2/2003 |
| WO | WO 03/015859 A2 | 2/2003 |

* cited by examiner

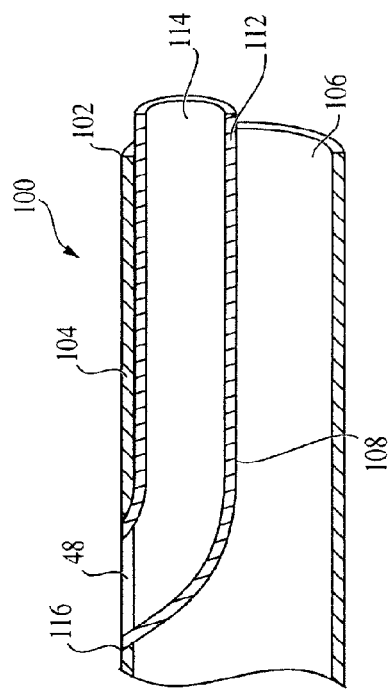
FIG. 4A
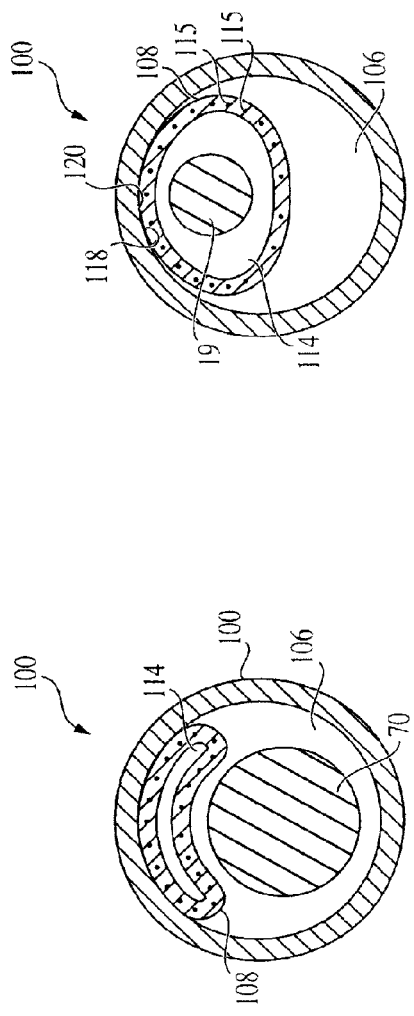
FIG. 4B
FIG. 4C

RAPID EXCHANGE CATHETERS USABLE WITH EMBOLIC PROTECTION DEVICES

This application is a continuation of U.S. Ser. No. 12/100,837, filed Apr. 10, 2008, which is a continuation of U.S. Ser. No. 12/021,008, filed Jan. 28, 2008, now abandoned, which is a continuation of U.S. Ser. No. 10/171,704, filed Jun. 14, 2002, now U.S. Pat. No. 7,717,934 B2, issued May 18, 2010, the contents of each of which are hereby incorporated herein by reference.

FIELD OF THE INVENTION

The present invention is related generally to intravascular medical devices. More specifically, the present invention is related to delivery and recovery catheters which can be used to deliver and recover embolic protection devices, including distal embolic protection filters.

BACKGROUND OF THE INVENTION

Coronary vessels, partially occluded by plaque, may become totally occluded by a thrombus or blood clot causing myocardial infarction, angina and other conditions. A number of medical procedures have been developed to allow for the removal of plaque from vessel walls or to clear a channel through the thrombus or clot to restore blood flow and minimize the risk of myocardial infarction. Carotid, renal, peripheral, and other blood vessels can also be blocked and require treatment. For example, atherectomy or thrombectomy devices can be used to remove atheroma or thrombus. Alternatively, in percutaneous transluminal coronary angioplasty (PTCA), a guide wire and guide catheter are inserted into the femoral artery of a patient near the groin, advanced through the artery, over the aorta, and into a coronary artery. An inflatable balloon is then advanced into the coronary artery, across a stenosis or blockage, and the balloon inflated to dilate the blockage and open a flow channel through the partially blocked vessel region. One or more stents may also be placed across the dilated region or regions. While some stenoses remain in place once dilated and/or stented, others are more brittle, and may partially crack and fragment after the dilation or stent placement, allowing the fragments to flow downstream where they may block more distal and smaller coronary vessels, possibly causing myocardial infarction, from that site. Consequences of embolization include stroke, diminished renal function, and impairment of peripheral circulation possibly leading to pain and amputation.

Saphenous vein grafts are often used to bypass occluded coronary vessels in coronary artery bypass surgery. With time, the grafts can become occluded with grumous. The grumous can also be dilated with balloons or removed in other ways. The grumous can present an even more difficult material to remove than thrombus, as the material is very friable, and likely to break into smaller fragments during the removal procedure.

Distal embolic protection devices have been developed to prevent the downstream travel of materials such as thrombi, grumous, emboli, and plaque fragments. Devices include occlusive devices and filters. Occlusive devices, for example distal inflatable balloon devices, can totally block fluid flow through the vessel. The material trapped by the inflatable devices can remain in place until removed using a method such as aspiration. However, aspiration cannot remove large particles because they won't fit through the aspiration lumen. Also, aspiration is a weak acting force and won't remove a particle unless the tip of the aspirating catheter is very close to the particle to be removed. During the occlusion, the lack of fluid flow can be deleterious. In coronary applications, the lack of perfusing blood flow can cause angina. In carotids, seizure can result from transient blockage of blood flow. In both coronaries and carotids it is not possible to predict who will suffer from angina or seizure due to vessel occlusion. If a procedure is started with an occlusive device, it may be necessary to remove it and start over with a filter device.

Some distal embolic protection devices include filters. Filters can allow perfusing blood flow during the emboli capture process. The filters can be advanced downstream of a site to be treated and expanded to increase the filter area. Emboli, such as grumous or atheroma fragments, can be captured in the filter until the procedure is complete or the filter is occluded. When the capacity of the filter is reached, the filter may then be retracted and replaced.

Distal embolic protection devices can be delivered over guide wires and within guide catheters. The distal embolic protection methods are normally practiced ancillary to another medical procedure, for example PTCA with stenting or atherectomy. The distal embolic protection procedure typically protects downstream regions from emboli resulting from practicing the therapeutic interventional procedure. In the example of PTCA, the treating physician must advance a guide wire over the aorta and into a coronary ostium. Advancing the guide wire through tortuous vessels from a femoral artery approach can be difficult, and vary with both the patient and the vessel site to be treated. Guide wires are typically selected by the treating physician, based on facts specific to the patient and therapeutic situation, and also on the training, experiences, and preferences of the physician. In particular, a physician may have become very efficient in using a specific guide wire to identify the left coronary ostium and then advance a balloon catheter over the positioned guide wire. The efficacy of the procedure may depend on the physician being able to use their favored guide wire.

The distal embolic protection device is preferably delivered using the same, favored guide wire. The phrases "distal embolic protection device" or "embolic protection device" are used herein to refer to embolic protection devices that are occlusive and/or filtering. The terms "distal embolic protection device" and "embolic protection device" are used interchangeably, as either may be used to protect a target site located either proximal to or distal to another treatment site. The term "embolic protection element" may be used generally to include both occlusive and filtering elements disposed near the distal region of a distal protection device shaft.

In the example PTCA procedure, a guide catheter extends proximally from the patient's groin area, and may be about 100 centimeters long, later having a 140 centimeter long guide wire proximal region extending from the guide catheter. The distal embolic protection device delivery catheter, nominally about 130 centimeters in length, can be advanced over the guide wire and within the guide catheter, until a short length of guide wire extends from both the guide catheter and delivery catheter. The guide wire can then be retracted and removed from the patient. In some methods, the distal protection device is then advanced through and out of the positioned delivery catheter, to the target site to be protected or filtered. In other methods, delivery is accomplished by disposing the distal embolic protection filter device within the delivery catheter distal region, and advancing the delivery catheter and embolic protection device together over the guide wire, and deploying the filter by retracting the delivery catheter while maintaining the position of the filter, thus forcing the filter distally out of the delivery catheter.

Advancement of the delivery catheter over a single length, nominally 130 centimeter long guide wire presents a problem. The treating physician can only advance the filter delivery catheter about 20 centimeters over the guide wire until the delivery catheter advances into the patient and the guide wire is inaccessible within the delivery catheter. The guide wire position should be controlled at all times so as to not be dislodged by the advancing delivery catheter from the hard acquired guide wire position within the patient.

One solution to this problem is to use a guide wire at least double the length of the delivery catheter. A 320 or 340 centimeter long guide wire can extend at least about 120 centimeters from the patient's groin, having an accessible region exposed at all phases of delivery catheter placement. However, the added length makes manipulating and rotating the guide wire very difficult for the treating physician. The extra length of the guide wire can be held by additional personnel to prevent the added wire length from falling to the floor, where it would become contaminated. However, not all cardiac catheter laboratories have personnel available to maintain control of the long guide wire. In many labs, the physician is working alone in the sterile field. Advancing a distal embolic protection device delivery catheter over a positioned, favored guide wire would be inherently more efficacious than requiring use of an unfamiliar, disfavored, or double length guide wire to position the delivery catheter.

With the distal filter in place, removal of the delivery catheter over the wire shaft of the distal filter device is ultimately desirable. If a single length, nominally 140 centimeter long, distal filter device shaft is extending about 20 centimeters proximally from the delivery catheter, a problem is presented. Once the delivery catheter is retracted about 20 centimeters, the proximal end of the wire would disappear into the proximal end of the retracting delivery catheter, and control of the distal filter device wire position lost. If the delivery catheter were further retracted, the retraction of the delivery catheter over the wire shaft may pull the distal filter device from its position. Again, a distal protection device having a double length wire shaft can be used. The double length wire shaft allows the delivery catheter to be retracted over the distal filter device shaft while presenting an exposed portion of the wire shaft at all times. As discussed with respect to the double length guide wire, the added length presents problems.

What would be desirable are distal embolic protection device delivery catheters that can be delivered over the single length guide wire favored by the treating physician and retracted over single length wire shafts of distal embolic devices.

SUMMARY OF THE INVENTION

The present invention provides improved delivery catheters which can be used to deliver and recover embolic protection devices, including distal embolic filter devices. The catheters are "rapid exchange" or "single operator exchange" catheters that can be delivered over a single length guide wire. The catheters can also be retracted over a single length distal embolic filter device wire shaft. Catheter assemblies and methods for using the assemblies are also provided.

A first catheter according to the invention is a two port catheter having two sidewall ports for receiving wires through the ports. One two port catheter includes a distal region, an intermediate region, and a proximal region for extending out of the patient's body. Some two port catheters include a tubular body having a tube sidewall and a lumen extending through the tube. The two port catheter can be formed of a tube over its entire length or be tubular only in the distal region, being formed of a shaft in the intermediate and proximal regions. The distal region can include a distal end port or distal tip port, a distal sidewall port, and a proximal sidewall port. The distal end port and the distal sidewall port can be dimensioned to allow passage of a guide wire. The proximal sidewall port can be dimensioned to allow passage of an embolic protection device wire shaft through the port. In a preferred embodiment, the distal end port, the distal sidewall port, and the proximal sidewall port are all dimensioned to allow passage of a 0.014" outside diameter wire through the ports. The catheter inside diameter can be dimensioned to allow passage of an embolic filter in a compressed state. Some catheters are formed of a tube extending from the distal end to the proximal end, while other catheters are formed of a tube in the distal region and a shaft or smaller tube in the intermediate and proximal regions. The present invention also includes catheter assemblies which can include a two port catheter, a guide wire, a distal embolic protection device, and a guide catheter adapted to receive the catheter within.

In use, a guide catheter can be advanced through the vasculature to a location near the ultimate target site to be filtered. A guide wire can be advanced through the guide catheter and further to a location nearer the target site or even distally past the target site.

A distal embolic protection device, for example, a distal embolic protection filter device having a distal filter element and elongate wire shaft, can be provided. The filter device can be disposed within the two port catheter such that the distal filter element lies between the distal sidewall port and the proximal sidewall port, with the wire shaft extending outwardly through the proximal sidewall port to extend proximally along the length of the catheter. In one method, the distal filter element is radially reduced in shape and advanced distally into the catheter through the proximal sidewall port. In a preferred method, the distal embolic protection device is back loaded into the catheter by threading the distal embolic protection device shaft proximal end into the catheter distal end port and out of the catheter proximal sidewall port. In some embodiments, the distal filter element lies within a bulge between the distal sidewall port and the proximal sidewall port.

The guide wire proximal end can be threaded into the catheter distal end port and out of the catheter distal sidewall port to extend proximally along the exterior of the catheter. The catheter carrying the distal embolic protection device can then be advanced distally over the guide wire to near the target site. In one method, the catheter is advanced across the target region while in other methods the catheter is advanced to a position proximal of the target region. The guide wire can then be proximally retracted, and pulled from within the catheter through the distal sidewall port. The distal filter element is then advanced distally out of the two port catheter distal end port and allowed to expand in some methods. In other methods, the distal filter element is held in a relatively constant position, while the catheter is retracted proximally away from the distal filter element, such that the distal filter element exits the catheter distal end port and is allowed to radially expand to filter blood in the vicinity of the target site.

When deemed desirable by the treating physician, the catheter can be proximally retracted from the patient by grasping the proximal end of the distal embolic protection device shaft while proximally retracting the catheter. As only a short length of the distal embolic protection device wire shaft extends through the catheter distal region, only a short added length of wire shaft is required, rather than a double length wire shaft as would be required by a conventional catheter. In some methods, the back loading of the guide wire through the distal end port and out of the distal sidewall port is aided by a collapsible guide wire tube extending from near the distal end port to the distal sidewall port. In other embodiments, the back loading of the guide wire is aided by a hinged flap or baffle which allows a distally advancing filter element to move the flap aside but which does not allow a proximally advancing guide wire to pass, rather directing the guide wire proximal movement outward towards the distal sidewall port.

After the therapeutic procedure the catheter may be used to recover the embolic protection device. To do so the proximal end of the embolic protection device shaft proximal end is threaded into the distal end port and out the proximal sidewall port. The catheter is advanced into the patient along the device shaft until the catheter tip is immediately proximal to the embolic protection device. At this point the embolic protection device may be partially or totally recovered into the lumen of the catheter by effecting relative motion between the device shaft and the catheter. Subsequently the catheter/embolic protection device can be withdrawn as a unit from patient's body.

Another catheter according to the present invention is a three port catheter, having three sidewall ports. The three port catheter can be formed of a tube over its entire length or be tubular only in the distal region, being formed of a shaft in the intermediate and proximal regions. The three port catheter can include a distal end port dimensioned to allow passage of a guide wire through the port, but not being large enough to allow passage of a filter element. The reduced size of the distal end port allows for a reduced profile catheter distal end, which can now be narrowly tapered to allow passage through smaller diameter vessels and past more highly stenosed vessel regions. The distal end port can also be tapered to perfectly match the guide wire so as to facilitate smooth passage across vessel irregularities such as calcium spicules or implanted stents. The three port catheter can include a distal sidewall port, an intermediate sidewall port, and a proximal sidewall port. The intermediate sidewall port can be dimensioned to allow passage of a guide wire through the port, and can function in a similar manner to the distal sidewall port described with respect to the two port catheter. In some catheters, the intermediate port is substantially circumferentially aligned with the distal sidewall port.

The proximal sidewall port in the three port catheter can be disposed opposite the distal sidewall port, and can be about 180° opposite the distal sidewall port. In other respects, the proximal sidewall port can serve the same function as the proximal sidewall port discussed with respect to the two port catheter. Specifically, the proximal sidewall port can allow passage of the distal embolic protection device wire shaft through the port. The distal sidewall port of the three port catheter can serve to allow passage of the distal embolic protection device filter through the distal sidewall port. The distal sidewall port can be a slit in some embodiments, a slot in other embodiments, and a round or oval opening in still other embodiments. The three port catheter is designed such that the distal embolic protection device filter element can be carried between the intermediate sidewall port and the proximal sidewall port, then forced distally through the distal sidewall port rather than through the distal end port as in the two port catheter. The distal sidewall port can thus be a slit which is forced open by the advancement of the filter element. Thus, only the distal sidewall port need be sufficiently large to allow passage of the filter, rather than the distal end port. In some three port catheters, the distal end port is disposed off center from the central longitudinal axis of the catheter while the distal sidewall port is substantially aligned with the central longitudinal axis of the catheter such that distal advancement of the filter element is directed substantially toward the distal sidewall port rather than the distal end port.

In use, the guide catheter and guide wire can be advanced to near the target site, as with the two port catheter. The distal embolic protection device can be back loaded through the distal sidewall port, with the wire shaft of the distal embolic protection device exiting the proximal sidewall port, leaving the filter element disposed within the catheter, preferably between the proximal sidewall port and the intermediate sidewall port. The guide wire proximal end can be threaded through the distal end port of the catheter to exit the intermediate port of the catheter. The preloaded catheter can be advanced to near the target site. In some methods, the guide wire is left in place after catheter placement to preclude the possibility of the filter element being forced into the distal end port. The filter element may also be provided without a wire tip to address the same problem. In a preferred method, the guide wire is retracted and the embolic protection filter body advanced distally out of the distal sidewall port. With the distal embolic protection device in position, the catheter can be proximally retracted from the patient. The distal embolic protection device wire shaft need only be slightly longer than the catheter, not twice as long, as only a short length of distal embolic protection device wire shaft lies within the distal region of the catheter.

After the therapeutic procedure the three port catheter can be used to recover the embolic protection device by threading the proximal end of the device shaft into the distal sidewall port, out the proximal or intermediate port, and proceeding as described for the two port catheter.

A third catheter according to the present invention includes a tube having a normally open slot extending along most of the tube length. The slotted catheter preferably has a distal end port dimensioned to allow passage of a guide wire and a distal embolic protection device filter through the port. The catheter preferably has a distal sidewall port to allow passage of a guide wire through the distal sidewall port. The distal sidewall port can, but need not, be formed as a widened or enlarged portion of the longitudinal slot extending through the sidewall. The catheter preferably has an unslotted distal most region to provide column strength for allowing the catheter to be pushed across narrowed, stenosed vessel regions. Some catheters include a funnel portion disposed near the proximal region to aid in introducing the distal embolic protection device filter into the lumen within the catheter.

The slot is preferably at least about 0.001" in width, and can be about 0.005" or even 0.014" in width. The slot is preferably dimensioned to inhibit the free, transverse movement of a guide wire or distal embolic protection device wire shaft through the slot. The catheter body is preferably sufficiently resilient to allow the forced, transverse movement of a wire shaft or guide wire through the slot when such movement is desired. The distal-most tip can be located off-center, with the center of the distal profile being occupied by the slot. The distal-most sidewall region can be curved or bent down to form an end wall containing the off-center, distal-most tip.

In use, a guide catheter can be advanced to near the target site, followed by the advancement of a guide wire, as with the two and three port catheters previously discussed. The guide wire proximal end can be threaded into the distal end port and out of the distal sidewall port, to extend along the outside of the catheter. The distal embolic protection device can be preloaded into the distal region of the slotted catheter. In some embodiments, the distal embolic protection device is front loaded by distally advancing the device into the proximal end of the catheter and further into the catheter distal region. In other methods, the distal embolic protection device is back loaded by proximally threading the distal embolic protection device wire shaft through the catheter distal end port and further proximally through the catheter until the wire shaft exits the proximal end of the catheter, and the filter element is disposed proximal of the distal sidewall port of the catheter.

The catheter carrying the distal embolic protection device can then be advanced over the guide wire to near the target site or across the stenosis. The guide wire can be proximally retracted from the catheter, followed by the deployment of the filter element through the catheter distal end port. When removal of the catheter is desired, the distal embolic protection device wire shaft can be forced transversely through the slot in the catheter beginning near the catheter proximal end. The wire shaft can be held substantially stationary, while the catheter is proximally retracted from the patient. The proximal retraction can be continued until the wire shaft is disposed within the distal sidewall port of the slot, whereupon the wire shaft can be grasped distal of the catheter distal end port and the catheter fully removed from the patient.

In a related method using the slotted catheter, the catheter can be advanced to across the stenosis or near the target site over the guide wire, with the catheter not yet carrying the distal embolic protection device. The distal embolic protection device can later be advanced through the lumen of the slotted catheter to the catheter distal region. The catheter can also be used to recover an embolic protection device as described for the two port catheter.

DESCRIPTION OF THE DRAWINGS

FIG. 4A is a fragmentary, side view of a catheter having a collapsible guide wire tube extending between the catheter distal end and the distal sidewall port;

FIG. 4B is an end view of the catheter of FIG. 4A, having a guide wire disposed within the collapsible guide wire tube;

FIG. 4C is an end view of the catheter of FIG. 4A, having the guide wire removed and the collapsible guide wire tube collapsed by the advancement of a distal embolic protection device filter;

DETAILED DESCRIPTION OF THE PREFERRED EMBODIMENTS

Figure 1:
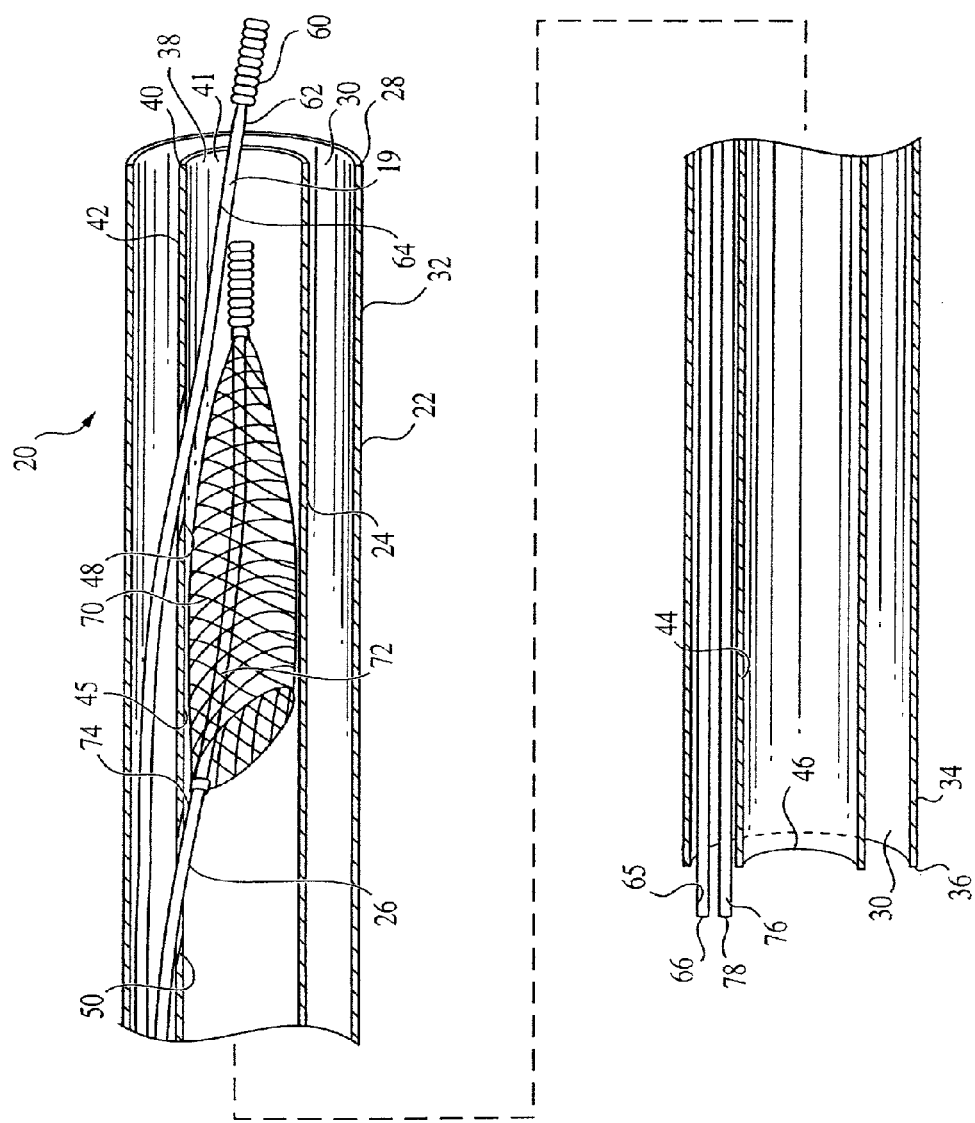
FIG. 1 is a highly diagrammatic, cut-away, side view of an assembly for delivering or recovering a distal embolic protection device, including a two-port catheter having a distal end port, a distal sidewall port, a proximal sidewall port, and having a guide wire disposed through the distal sidewall port, and a distal embolic protection device wire shaft extending through the proximal sidewall port, the catheter being disposed within a guide catheter.

FIG. 1 illustrates a distal embolic protection device assembly 20 which can be used to deliver a distal embolic protection device to a target site within the vasculature. Assembly 20 includes a delivery/recovery catheter 24 disposed within a guide catheter 22. The delivery/recovery catheter can be used to both deliver and recover a distal embolic protection filter. The term "delivery catheter", as used herein, should be understood as including a delivery catheter that can also be used to recover a particulate containing filter. Delivery catheter 24 includes a guide wire 19 and a distal embolic protection device 26 disposed within. The proximal end of assembly 20 is illustrated without any hub or Luer fitting to more clearly illustrate the invention. In a preferred embodiment, a hub, well known to those skilled in the art, can be affixed to the assembly proximal end to form a fluid-tight seal about the protruding members. Delivery catheters referred to in the present application preferably have no added therapeutic distal devices. Specifically, delivery catheters preferably are single lumen catheters and have no inflatable or expandable balloons, distal atherectomy burrs, water jet devices, or the like. Some delivery catheters can be coated with therapeutic coatings however, including anti-thrombogenic coatings, for example heparin, or with lubricious coatings, for example, hydrogels or silicone.

Guide catheter 22 includes a distal end 28, a distal region 32, a proximal region 34, a proximal end 36, and a lumen 30 extending therethrough. Guide catheters are well known to those skilled in the art and will not be further explained. Delivery catheter 24 can be referred to as a "two-port" catheter, as it has two sidewall ports. Delivery catheter 24 includes a distal end 40, a distal region 42, a distal port or distal sidewall port 48, a proximal port or proximal sidewall port 50, a proximal region 44, a proximal end 46, and a lumen 38 extending therethrough. In some embodiments, proximal region 44 of delivery catheter 24 is formed by a shaft rather than a tube, with catheter lumen 38 extending through only a distal region of the delivery device. Delivery catheter 24 also includes a distal end port or distal tip port 41, formed at the distal end of the catheter. In one embodiment, proximal region 44, which is proximal of proximal port 50, can be formed by a tube which has been transversely slit and pressed downward proximal of proximal port 50. Guide wire 19 may be seen to include a distal tip 60, a distal region 62, a wire or shaft 64, a proximal region 65, and a proximal end 66. Guide wire 19 may be seen to extend proximally from distal tip 60, within catheter lumen 38, then extending outwardly through distal sidewall port 48 to extend proximally along the outside of delivery catheter 24.

Referring again to FIG. 1, it may be seen that guide wire 19 has been threaded through delivery catheter distal sidewall port 48. In some methods, guide wire 19 is advanced through guide catheter 22, with guide wire proximal end 66 yet to be threaded into delivery catheter distal end port 41 and out delivery catheter distal sidewall port 48. In this method proximal end 66 of the guide wire is threaded into distal end 41 of the catheter and out through distal sidewall port 48. This is referred to as "back loading". The wire back loading can be aided by arcing the distal region of delivery catheter 24, such that the guide wire proximal end 66 is pressed against the inner wall of the catheter near distal sidewall port 48. In some embodiments, other assistance is given to back loading the guide wire into the delivery catheter and through the delivery catheter distal sidewall port. Distal embolic protection device 26 may be seen to include a shaft or wire 74 including a distal region 72 coupled to a distal filter 70.

Distal filter 70 can be viewed as one type of distal emboli protection element. Other distal protection elements which can be included as part of the present invention are occlusive emboli protection elements, including expandable or inflatable elements for blocking fluid flow through a vessel. Unless otherwise indicated, occlusive elements should be considered as interchangeable with filter elements in the present invention.

Distal embolic protection device shaft 74 may be seen to have a proximal region 76 and a proximal end 78 extending proximally from guide catheter 22. Filter 70 is shown in a compressed, radially reduced profile configuration as a result of disposition within delivery catheter 24. In a preferred embodiment, filter 70 is biased to expand radially outward when not constrained by delivery catheter 24. Distal embolic protection device filter 70 may be seen disposed between proximal sidewall port 50 and distal sidewall port 48 in intermediate region 45. Distal embolic protection device shaft 74 may be seen to lie within catheter lumen 38 distal of proximal port 50, then extend through proximal port 50 to the exterior of delivery catheter 24, then extend along the outside of delivery catheter 24 over its length.

In one assembly, guide wire 19 is formed of stainless steel or Nitinol and has a safety, spring tip. Guide wire 19 can have a length of between about 130 and 180 cm. in some embodiments. Guide wire 19 can have radiopaque marker bands along its length. Guide wire 19 may also have an outside diameter of between about 0.009 and 0.035 inches in some embodiments, and about 0.014 inches in a commonly used embodiment. Delivery catheter 24 can be formed of materials well known to those skilled in the art. In one embodiment, the distal region of catheter 24 is formed of a softer, more pliable material than the more proximal regions of the catheter. In one embodiment, catheter distal region 42 is formed of a rather floppy, soft material. In one catheter, the distal region is formed of a polymer such as LDPE, MDPE, or PEBAX. This floppy distal region can be coupled to stiffer intermediate and proximal regions formed of polymers such as HDPE, VESTAMID, or Polyimide. The floppy distal region can provide a distal region better adapted to advance through tortuous vessels while the more rigid intermediate and proximal regions can provide pushability.

Distal embolic protection device 26 is preferably an expandable filter device. Filter 70 is well known to those skilled in the art and can be a filter as disclosed in U.S. Pat. No. 6,325,815, European Patent Application No. 1181900 A2, and PCT Pub. No. WO 96/01951, all herein incorporated by reference. In one example of the invention, distal embolic protection device shaft 74 is formed of stainless steel and has an outside diameter of about 0.014 inches.

In one embodiment, the distance between delivery catheter distal sidewall port 48 and distal end 40 is between about 5 and 30 cm. In another embodiment, proximal sidewall port 50 is located at a distance of between about 15 and 50 cm. from distal end 40. In some catheters according to the present convention, distal sidewall port 48 is located between about 5 and 20 cm. distal of proximal sidewall port 50, and the delivery catheter can be about 3 Fr. in diameter and about 135 cm long. From inspection of FIG. 1, it may be seen that guide wire 19 is within lumen 38 only over its length between catheter distal end 40 and catheter distal sidewall port 48. When advancing delivery catheter 24 over guide wire 19, only the added length between catheter distal end 40 and distal sidewall port 48 need be added to guide wire 19, rather than doubling its length. Inspection of FIG. 1 also illustrates that distal embolic protection device shaft 74 is only within lumen 38 of catheter 24 over the length between catheter distal end 40 and proximal sidewall port 50. When delivery catheter 24 is retracted over distal embolic protection device shaft 74, only the wire length between catheter distal end 40 and proximal sidewall port 50 need be added to the shaft 74 length, rather than doubling its length. Both distal port 48 and proximal port 50 may be formed as "skives" to aid in threading the guide wire and distal embolic protection device wire shafts through the respective ports and to allow a low entry angle (less than about 5 or 10 degrees) between the guide wire or shaft axis and the catheter axis so as to minimize sliding friction between the two.

Ports 48 and 50 can both be skived and dimensioned to allow a distally and inwardly extending wire to penetrate into the tube lumen at an angle of less than about 10 degrees in some embodiments and less than about 5 degrees in other embodiments. Some skived ports have a proximal port sidewall region than is cut at an angle of less than about 10 degrees or even 5 degrees to support the shallow entry angle. In some embodiments, both the port proximal and distal sidewall portions are cut at an angle of less than about 10 or 5 degrees. The port longitudinal dimension is preferably the largest dimension of the skived ports, which can be oval or elongate in shape, to provide for a shallow entry angle. The port also has a transverse dimension orthogonal to the catheter longitudinal axis. The port transverse dimension is preferably sized to allow low friction guide wire passage. Unless otherwise stated, all sidewall ports in the present application used to receive guide wires or shafts of embolic protection devices can be skived and have a shallow entry angle of less than about 10 or 5 degrees.

Figure 2:
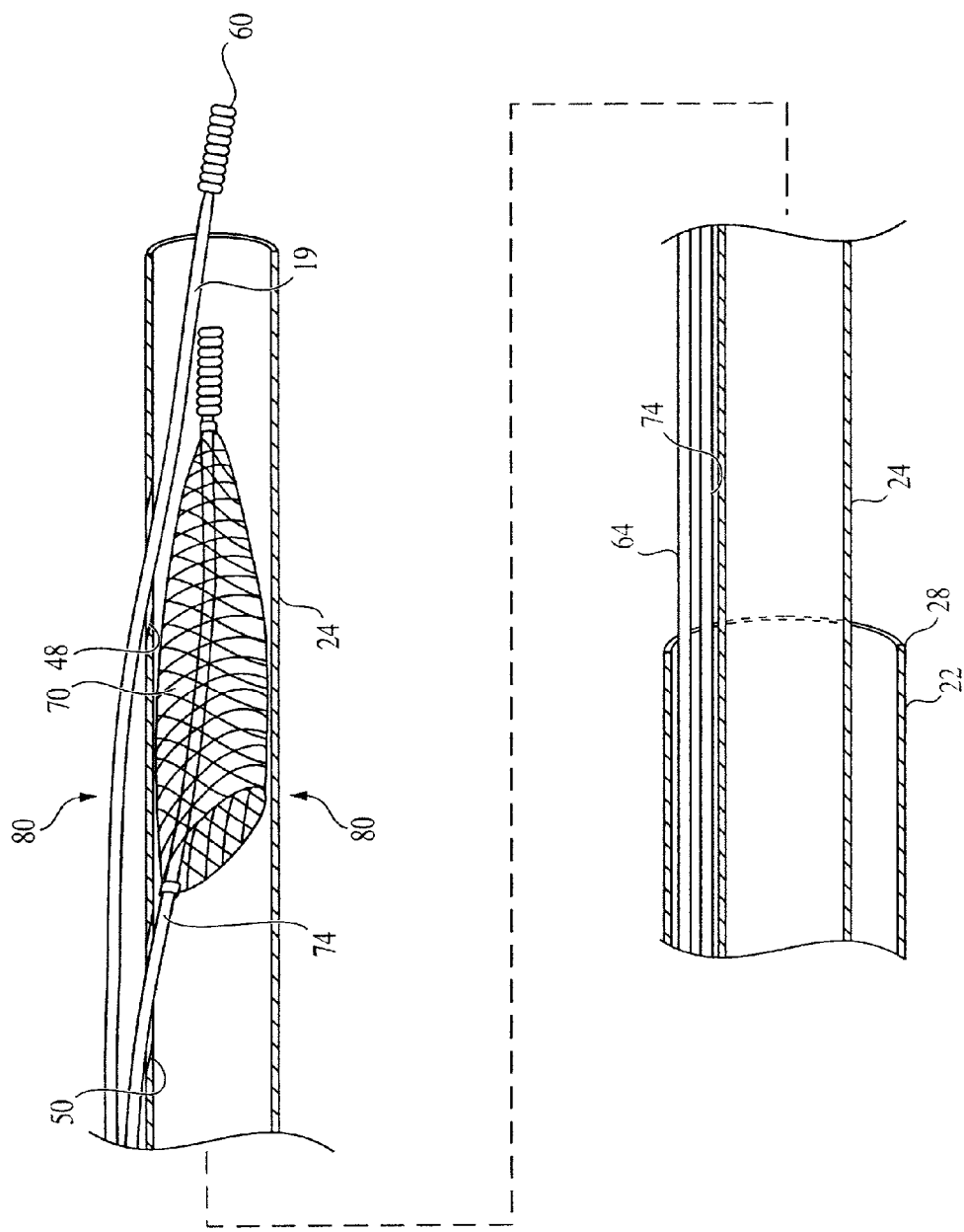
FIG. 2 is a highly diagrammatic, cutaway side view of the assembly of FIG. 1, after the catheter has been advanced distally from the guide catheter, and the guide wire advanced distally from the catheter.

FIG. 2 illustrates delivery catheter 24 after the catheter has been advanced distally from guide catheter 22. Guide wire distal tip 60 has been advanced further distally from delivery catheter 24. In some methods, guide wire 19 is advanced distally through guide catheter 22, followed by the advancement of delivery catheter 24 over guide wire 19. Guide wire 19 can be advanced ahead of delivery catheter 24, and delivery catheter 24 advanced over guide wire 19. This process can be repeated until the guide wire and the delivery catheter have been advanced to the target site. In other methods, guide wire 19 and delivery catheter 24 can be advanced together across the target site. Guide wire 19 can provide stiffening for delivery catheter 24. In some methods guide wire 19 is retracted, and distal embolic protection device 26 is then advanced through delivery catheter 24. In some methods, the guide wire crosses a lesion, followed by the delivery catheter. In other methods, the delivery catheter and guide wire together are advanced across a lesion. As indicated in FIG. 2 filter 70 has been positioned at the target site, indicated at 80. With distal embolic protection device filter 70 in the desired position, guide wire 19 can be retracted.

Figure 3:
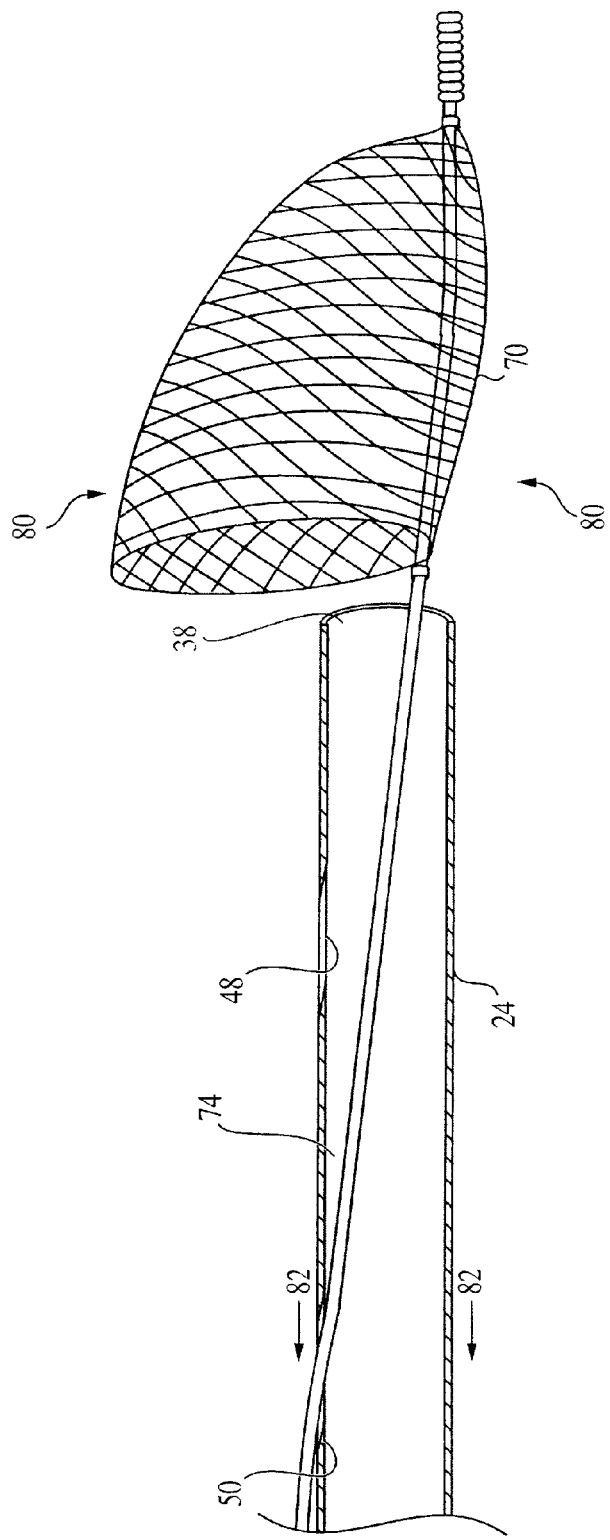
FIG. 3 is a fragmentary, side view of the catheter of FIG. 2, after the guide wire has been proximally retracted from the catheter and the catheter proximally retracted to expose the distal embolic protection device filter.

FIG. 3 illustrates delivery catheter 24, after guide wire 19 has been retracted proximally through distal sidewall port 48. With guide wire 19 no longer present within catheter lumen 38, distal embolic protection filter 70 can be distally advanced from delivery catheter 24. In a preferred embodiment, as indicated at 80 and by arrows 82, delivery catheter 24 is proximally retracted, while distal embolic protection filter 70 is held in place by the treating physician grasping and holding the distal embolic protection device shaft proximal region. By retracting delivery catheter 24, distal embolic protection filter 70 is allowed to expand radially, and preferably expands to provide filtration across the entire cross sectional area of the vessel. With distal embolic protection filter 70 in place, in some methods, delivery catheter 24 can be retracted from the patient. In other methods, delivery catheter 24 can remain in place, and a partially filled filter 70 later retracted partially into the catheter to close the filter mouth, and both filter and delivery catheter retracted from the patient. In still other methods, delivery catheter 24 can be retracted from the patient, an interventional procedure performed over device shaft 74, and delivery catheter 24 re-introduced over the shaft to recover the filter by closing the filter mouth.

Figure 4:
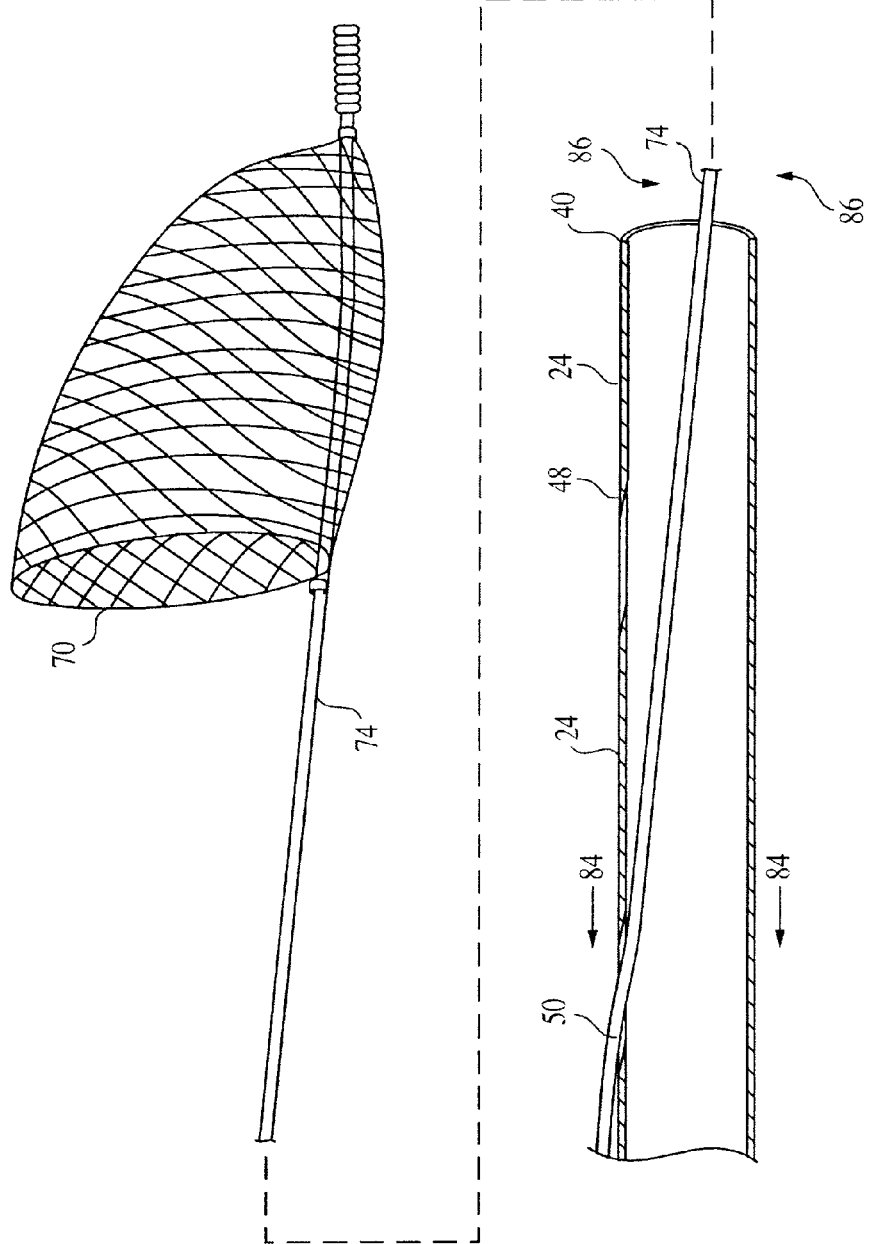
FIG. 4 is a fragmentary side view of the distal embolic protection device and catheter of FIG. 3, with the catheter being retracted over the distal embolic protection device wire shaft.

FIG. 4 illustrates distal embolic protection device filter 70, with delivery catheter 24 being proximally retracted as indicated by directional arrows 84. When catheter distal end 40 has been fully retracted from the patient, distal embolic protection device shaft 74 is exposed, as indicated at 86, and can be grasped by the treating physician, leaving only a length between catheter distal end 40 and catheter proximal sidewall port 50 unavailable for grasping. With distal embolic protection device shaft 74 grasped at 86, delivery catheter 24 can be fully retracted from device shaft 74. As can be seen from inspection of FIG. 4, only the added length between catheter distal end 40 and catheter proximal sidewall port 50 need be added to distal embolic protection device shaft 74, rather than doubling its length.

FIG. 4A illustrates one delivery catheter 100 having a distal end or tip 102, a distal region 104 and a lumen 106 extending therethrough. Delivery catheter 100 further has a collapsible tube 108 disposed within catheter lumen 106. Collapsible tube 108 can serve as collapsible guide wire tube extending between catheter distal end 102 and distal sidewall port 48. Collapsible tube 108 includes a distal end 112 and a lumen 114 extending therethrough. Collapsible tube 108 preferably extends distally of the delivery catheter distal end and may be of a contrasting color to facilitate identification of the collapsible tube distinct from the delivery catheter. Tube 108 further includes a proximal region 116 which can be bonded to the catheter sidewall near distal sidewall port 48 to provide an exit for the guide wire. Distal sidewall port 48 preferably has a skived configuration.

FIG. 4B illustrates delivery catheter 100 in an end view. Delivery catheter 100 has collapsible tube 108 within. Collapsible tube 108 is shown in the open position, having guide wire 19 extending therethrough. Collapsible tube at 108 has a tube wall outer surface 118 facing a catheter tubular wall inner surface 120. Collapsible tube outer surface 118 can be bonded to catheter wall inner surface 120. Suitable bonding methods including adhesives, and heat and solvent welding may also be used to attach collapsible tube 108 to catheter 120. Longitudinal stiffening members 115 may be included in the collapsible wall. Guide wire 19 may be seen extending through collapsible tube lumen 114. Guide wire 19 may extend proximally through the tube and out distal sidewall port 48. Collapsible tube 108 preferably has sufficient column strength to guide a back loaded guide wire, while being radially weak to collapse and allow passage of a filter. In use, the proximal end of guide wire 19 can be inserted into collapsible tube distal end 112, and pushed proximally until the guide wire proximal end extends through distal sidewall port 48. Collapsible tube 108 thus aids in back loading guide wire 19 through delivery catheter 100.

FIG. 4C illustrates delivery catheter 100 having guide wire 19 retracted from collapsible tube 108. Collapsible tube 108 is shown in its collapsed position. Distal embolic protection device filter 70 has been forced distally forward from its parked position proximal of distal sidewall port 48. Distal embolic protection device filter 70 has thus forced part of collapsible tube 108 aside, collapsing the collapsible tube. Distal embolic protection device filter 70 may then be distally advanced from the delivery catheter. Collapsible tube 108 may be made of any suitable, collapsible polymer, well known to those skilled in the art. Some collapsible tubes are formed of LDPE, while other collapsible tubes are formed of PEBAX, nylon, or polyurethane. Preferably, the collapsible tube is formed of elastomeric polymer such as polyurethane, silicone, latex, and the like.

Figure 4D:
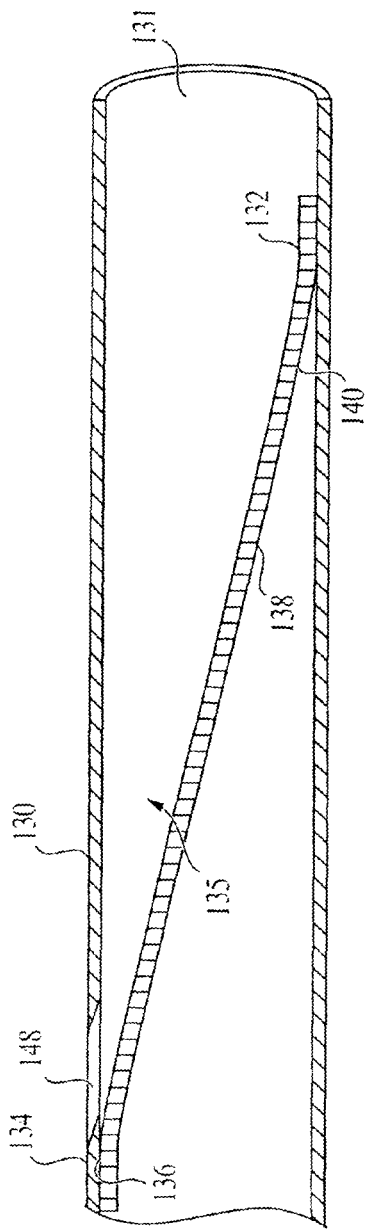
FIG. 4D is a fragmentary, side view of another catheter having a hinged baffle for directing a proximally back loading guide wire through the distal sidewall port while moving aside to allow distal passage of a distal embolic protection device filter.

FIG. 4D illustrates another delivery catheter, catheter 130. Delivery catheter 130 includes a distal end port 131, a sidewall 134, and a distal sidewall port 148. Delivery catheter 130 has a hinged flap 132. Hinged flap 132 can be fixedly secured to catheter sidewall 134 just proximal of distal sidewall port 148, as indicated at 136. The hinged flap can be a round flap having a tab for bonding to the sidewall, and any suitable bonding method, for example, solvent welding, adhesive, or heat bonding can be used to affix flap 132 to sidewall 134. Sidewall port 148 can also be skived to ease in threading a guide wire through the port. Flap 132 includes a central portion 138 and an extreme end portion 140 which is opposite of bonded portion 136. As indicated by arrow 135, hinged baffle or flap 132 can be forced aside by an advancing distal embolic protection device filter. In the position shown in FIG. 4D, a guide wire can be inserted through catheter distal end port 131 until encountering flap 132. The guide wire proximal end will then be forced along flap 132 and guided to sidewall port 148. Hinged baffle or flap 132 thus aids in back loading a guide wire through a catheter distal end port and out through the distal sidewall port. The hinged baffle or flap 132 can be formed of any suitable material. Exemplary materials include HDPE, PEBAX, nylon, polyimide, PEEK, or liquid crystal polymer.

Figure 5A:
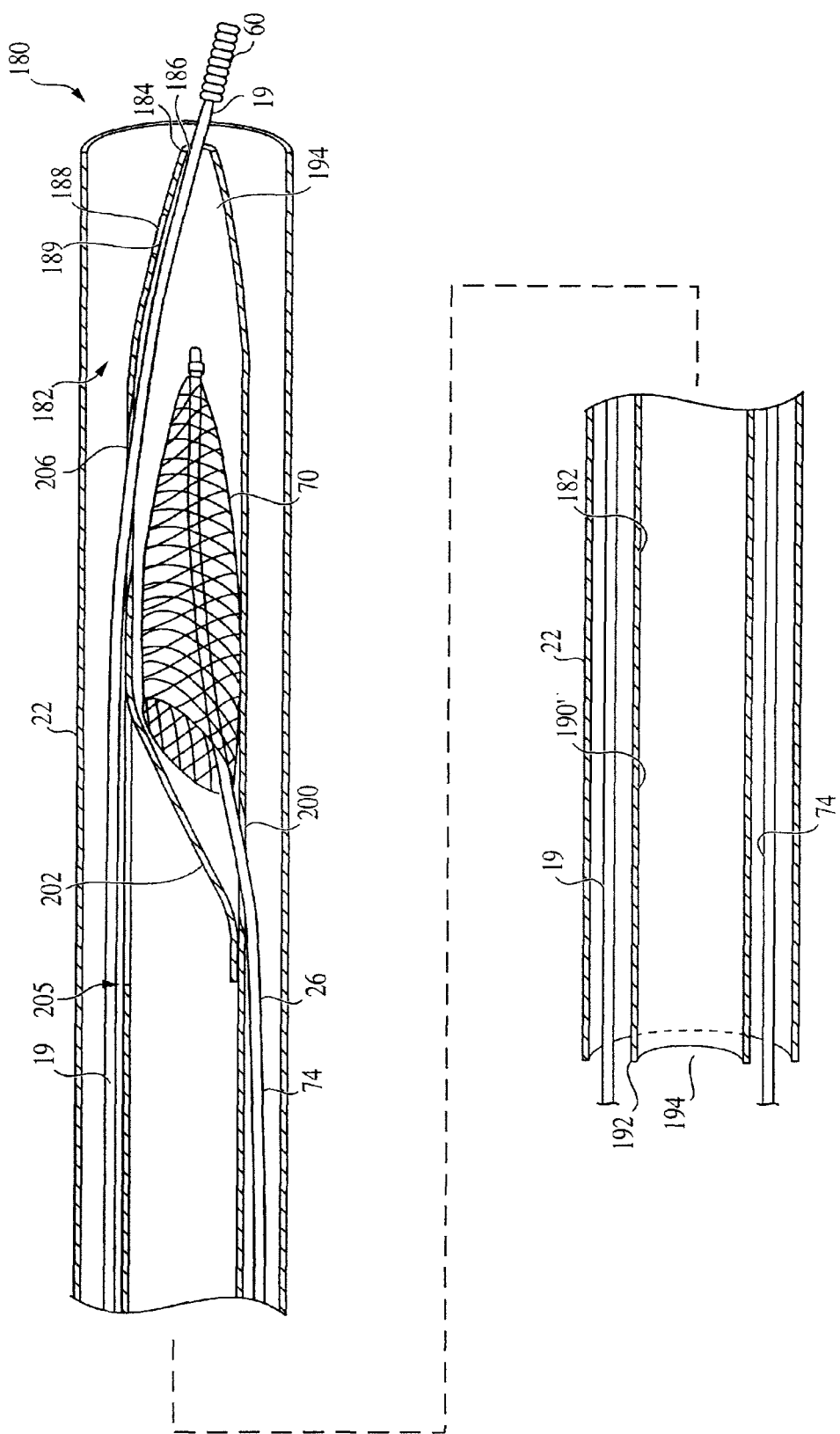
FIG. 5A is a fragmentary, cut-away, side view of a guide catheter, guide wire, and distal embolic protection device as in FIG. 1, including a three-port catheter having a distal sidewall port for admitting a distal embolic protection device filter, a intermediate sidewall port for admitting a guide wire, and a proximal sidewall port for admitting a distal embolic protection device shaft or wire.

FIG. 5A illustrates another distal embolic protection device delivery assembly 180 including another embodiment of delivery catheter in a three-port delivery catheter 182, having guide wire 19 disposed partially within, having distal embolic protection device 26 also disposed partially within, and being disposed within guide catheter 22. Guide wire 19, distal embolic protection device 26, and guide catheter 22 are as previously described with respect to FIG. 1. Delivery catheter 182 may be seen to have a distal end 184 having a distal end port 186 disposed therein. Delivery catheter 182 further has a distal region 188, a proximal region 190, a proximal end 192, and a lumen 194 extending therethrough. As previously discussed, in some embodiments, catheter 182 may be formed of a shaft in the proximal region 190.

Delivery catheter 182 may be seen to include a distally tapering outer diameter over distal region 188. The distally tapering region can act to more closely approach guide wire 19, and provide support for the guide wire. The distal taper can also act to decrease any gap between guide wire 19 and the inner wall of catheter distal end 184. In the two-port delivery catheter 24 of FIG. 1, distal end port 41, is large enough to pass the filter. In contrast, distal end port 186 need only be large enough to pass a guide wire, for example a 0.014 inch O.D. guide wire. The smaller profile of delivery catheter distal end 184 can significantly reduce the likelihood of catheter 182 snagging or hanging up on a stent or on a stenosed vessel region to be crossed.

Delivery catheter distal region 188 also includes a distal sidewall port 189 for admitting a distal embolic protection device filter therethrough. In some embodiments, distal sidewall port 189 has a round or oblong or oval shape. In other embodiments, distal sidewall port 189 is formed as a slit or slot which can expand to allow passage of an advancing distal embolic protection device filter therethrough. In some embodiments, distal sidewall port 189 is formed as a slit having a strain relief hole at either end.

Delivery catheter 182 also includes a proximal sidewall port 200. Proximal sidewall port 200 can be dimensioned to allow passage of distal embolic protection device shaft 74. In some embodiments, proximal sidewall port 200 is also large enough to admit passage of filter 70. Port 200 can be skived and dimensioned to receive a guide wire at a shallow entry angle, as previously discussed with respect to other sidewall ports.

In the embodiment illustrated, a flap or ramp region 202 is disposed just proximal of proximal sidewall port 200. Ramp or flap 202 can act to guide a back loaded distal embolic protection device shaft proximal end through proximal sidewall port 200 as the shaft is advanced proximally through delivery catheter 182, being forced or guided to exit the catheter lumen 194 through proximal sidewall port 200. Ramp or flap 202 need not be hinged, and can be fixed, in embodiments where a continuous lumen through the delivery catheter is not required. As previously described, catheter 182 can be formed as a shaft proximal of proximal sidewall port 200.

Figure 5B:
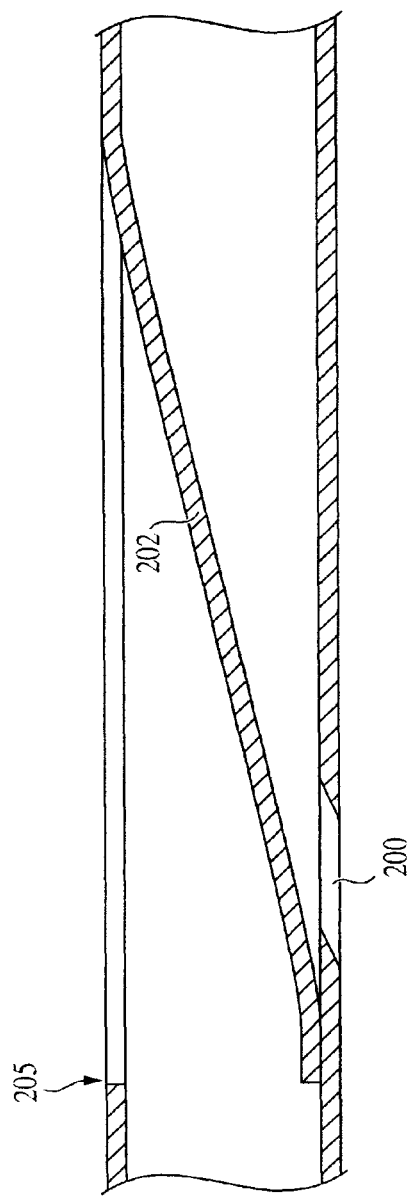
FIG. 5B is a detailed view from FIG. 5, having a collapsed tubular wall or ramp portion to direct a back loaded distal embolic protection device wire shaft through the proximal sidewall port.

FIGS. 5A and 5B illustrate one embodiment of delivery catheter sidewall port 200 having ramp 202 formed by making a slit 205 through the tube wall of the catheter, then collapsing the tube wall to form ramp 202, just proximal of proximal sidewall port 200. The collapsed tubular wall can be held in place through any suitable adhesive or bonding method. The collapsed tube wall thus forms a ramp, which can be used to guide a back loaded distal embolic protection device shaft through proximal sidewall port 200. Alternatively, the lumen can be filled by a solid cylinder with a bias cut end and the cylinder bonded in place.

Referring again to FIG. 5A, delivery catheter 182 also includes an intermediate sidewall port 206, disposed between distal sidewall port 189 and proximal sidewall port 200. As may be seen from inspection of FIG. 5A, distal sidewall port 189 can be disposed on the opposite side of delivery catheter 182 from proximal sidewall port 200. Proximal sidewall port 200 can thus be located 180° away from distal sidewall port 189. In some embodiments, intermediate sidewall port 206 is substantially aligned with distal sidewall port 189. Intermediate sidewall port 206 can be dimensioned to receive guide wire 19 therethrough. In some embodiments, intermediate sidewall port 206 is skived, as previously discussed with respect to other wire admitting sidewall ports In one embodiment, distal sidewall port 189 is located between about 0.2 and 5.0 centimeters from catheter distal end 184. Intermediate sidewall port 206 can be located between about 5 and 30 centimeters from distal end 184. Proximal sidewall port 200 can be located between about 15 and 50 centimeters from catheter distal end 184. In some embodiments, distal sidewall port 189 and proximal sidewall port 200 are disposed between about 5 and 20 centimeters apart.

In use, assembly 180 can be similar in many respects to assembly 20, discussed with respect to FIG. 1. Guide wire 19 can be advanced through guide catheter 22 to the target site, as previously discussed. Guide wire 19 can be threaded through catheter distal end port 186, exiting the delivery catheter through intermediate sidewall port 206, then running along the exterior of the delivery catheter to beyond the catheter proximal end. In some methods, guide wire 19 is front loaded through delivery catheter 182 by forcing guide wire distal tip 60 distally through intermediate sidewall port 206 then out delivery catheter distal end port 186. The catheter can thus be threaded over the guide wire but remain outside of the patient until the combination is jointly advanced to a region of interest.

Distal embolic protection device 26 can have the proximal end of distal embolic protection device shaft or wire 74 proximally back loaded through distal sidewall port 189, with distal embolic protection device filter 70 in a compact configuration and pulled proximally toward proximal sidewall port 200. In other embodiments, distal embolic protection device filter 70 is advanced or front loaded through proximal sidewall port 200 to the "parked" position between proximal sidewall port 200 and intermediate sidewall port 206.

Guide catheter 22 can be advanced to a coronary ostium, or other location. Guide wire 19 can then be advanced through the guide catheter and further to a target site to be protected. In some methods, the guide wire proximal end can be threaded through catheter distal end port 186 and out intermediate sidewall port 206. Delivery catheter 182, carrying distal embolic protection device 26, can be advanced over guide wire 19 distally from guide catheter 22 and beyond the site to be protected. With delivery catheter 182 and carried distal embolic protection device 26 in position, guide wire 19 can be proximally retracted, as previously discussed.

Figure 6:
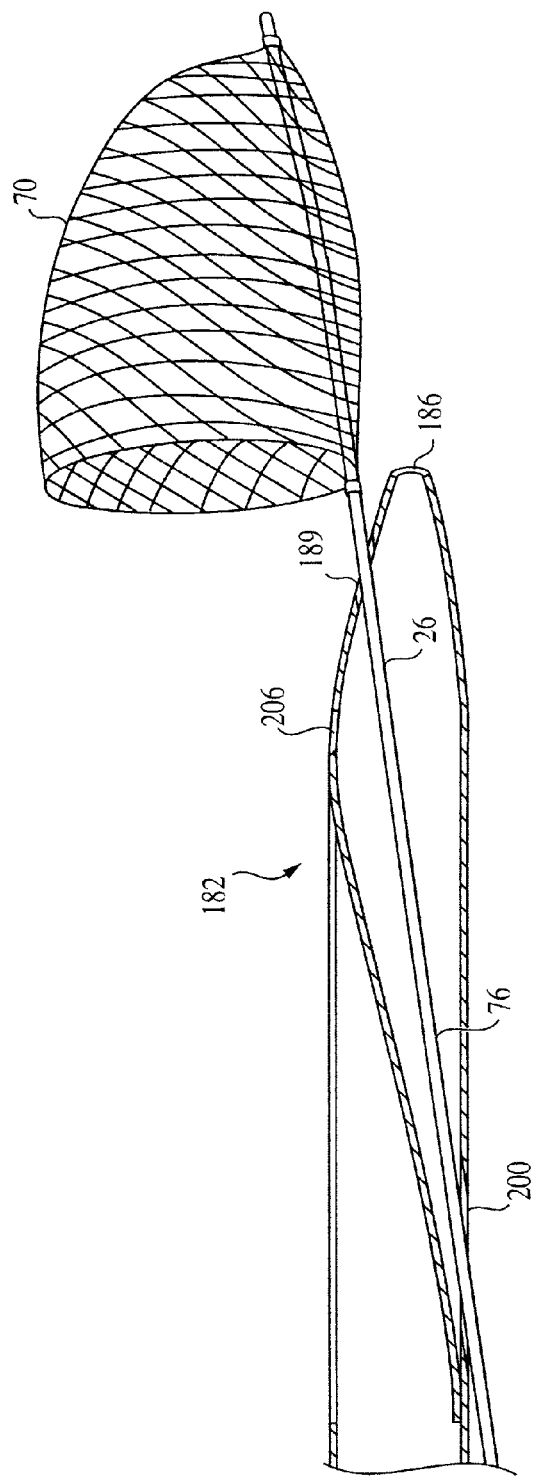
FIG. 6 is a fragmentary side view of the catheter of FIG. 5, being advanced distally from the guide catheter, having the guide wire proximally retracted, and having the distal embolic protection device filter advanced distally through the distal sidewall port.

FIG. 6 illustrates delivery catheter 182, after guide wire 19 has been proximally retracted through intermediate port 206. Distal embolic protection device 26 can be distally advanced through distal sidewall port 189, thus exiting delivery catheter 182. In some methods, delivery catheter 182 is proximally retracted, while maintaining the position of distal embolic protection device filter 70. With distal embolic protection device filter 70 in position, and suitably expanded to filter particulates, delivery catheter 182 can be proximally retracted over distal embolic protection device shaft or wire 76. As may be seen from inspection of FIG. 6, only the length of distal embolic protection device shaft 76 between proximal sidewall port 200 and distal sidewall port 189 is disposed within delivery catheter 182. This requires only a small added length to distal embolic protection device shaft 76 to effect catheter removal from shaft 76, rather than doubling the shaft length. In some embodiments, a suitable ramp or bump within delivery catheter 182 can further guide distal embolic protection device filter 70 through distal sidewall port 189. In some embodiments, a hinged flap or baffle, similar in some respects, but not others, to the hinged baffle described with respect to FIG. 4 can be used. In this embodiment, the hinged baffle can allow proximal movement of a back loaded guide wire through distal end port 186 while resisting distal movement of distal embolic protection device 70 against the flap. In some methods, the distal embolic protection device has no long distal tip, for example, no 0.014 inch O.D. wire tip, as the tip may try to exit distal end port 186. In other methods, the guide wire is left within distal end port 186, in order to prevent the filter body from attempting to exit the distal end port.

Figure 7A:
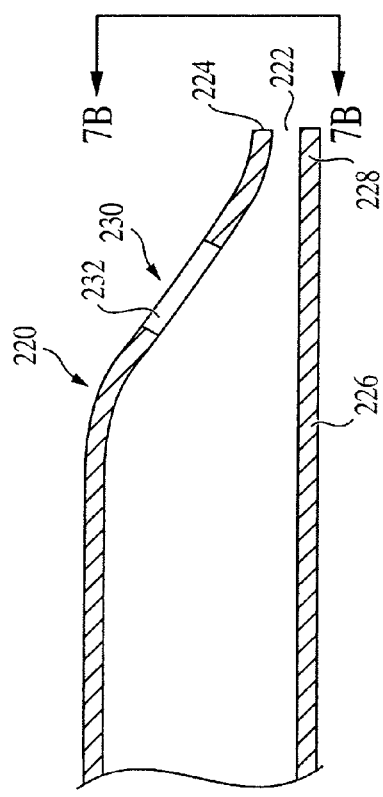
FIG. 7A is a fragmentary, longitudinal, wafer view of one embodiment of three port catheter, similar in some respects to the catheter of FIG. 5, having an off-center distal end guide wire port and an axially accessible distal end sidewall port for allowing passage of a distal embolic protection device filter.

FIG. 7A illustrates one embodiment of delivery catheter 220 having a distal region 226 which is asymmetric, having a substantially straight portion 228 and a tapering portion 230. Tapering portion 230 has a distal sidewall port, slit or slot 232 therethrough. A distal end port 222 is disposed within distal end 224 of delivery catheter 220. In some embodiments, distal end port 222 is dimensioned to accept a guide wire therethrough, but not a distal embolic protection device filter. This can act to prevent unwanted attempted or partial distal passage of a distal embolic protection device filter through distal end port 222. Distal end port 222 is preferably located off-center from the central longitudinal axis of the delivery catheter 220. In some embodiments, slit 232 is located to be axially aligned with the longitudinal central axis of the delivery catheter 220.

Figure 7C:
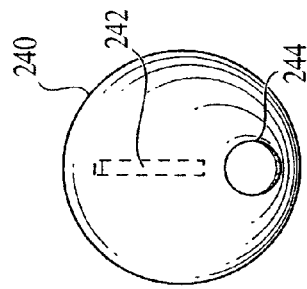
FIG. 7C is an end view of a catheter having regions of preferential tearing forming a distal sidewall port.
Figure 7B:
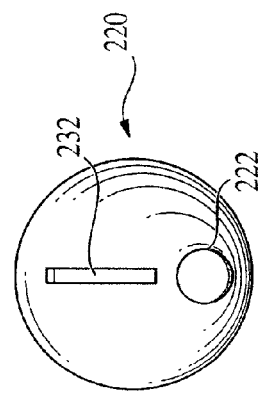
FIG. 7B is an end view of the catheter of FIG. 7A.

FIG. 7B illustrates delivery catheter 220, viewed from the distal end. The off-center location of distal end port 222 and the downwardly slanting orientation of distal sidewall port 232 toward distal end port 222 may also be seen. Distal sidewall port 232 may also be described as being accessible from the delivery catheter distal end when approached along the central longitudinal axis through the catheter, either from within the catheter or from the distal end of the catheter. The orientation of distal sidewall port 232 can allow a distal embolic protection device filter to be more easily distally forced from catheter 222 and out distal sidewall port 232.

FIG. 7C illustrates another embodiment of delivery catheter in catheter 240. Delivery catheter 240 is similar in some respects to delivery catheter 220, discussed with respect to FIGS. 7A and 7B. Delivery catheter 240 includes a "tearable" distal sidewall port 242 and a distal end port 244. Distal sidewall port 242 can be formed as a region of preferential tearing or weakness. The preferential tearing can be formed by perforating the sidewall of the catheter or cutting partially through the sidewall of the catheter, such that a distal embolic protection device being advanced distally against the region of preferential tearing can be forced through the preferential tearing region and out of the delivery catheter. In some embodiments, the preferential weakness of the distal sidewall port and/or the distal end port can be formed by making the catheter with an extremely thin wall in the regions to be torn.

Figure 8:
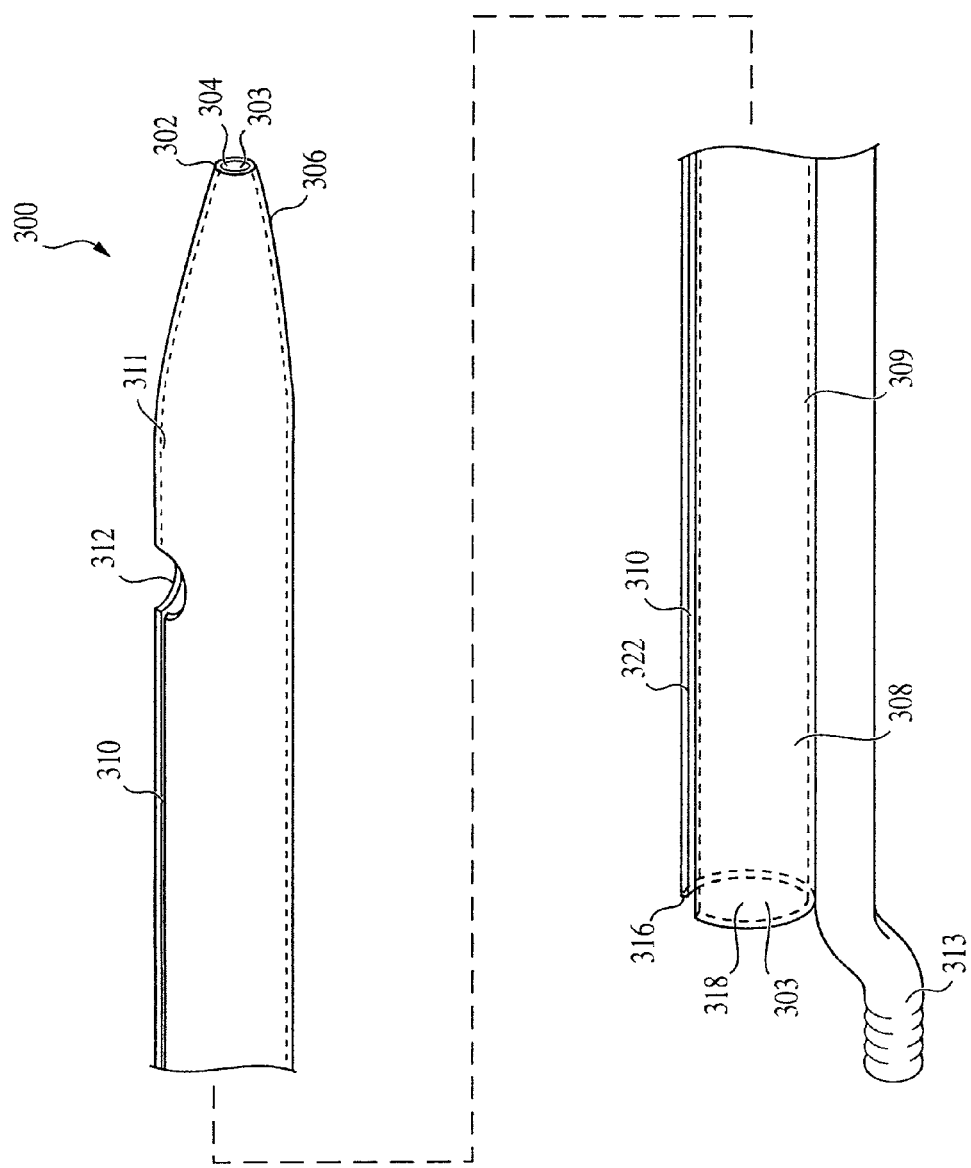
FIG. 8 is a fragmentary, highly diagrammatic, perspective view of a slotted catheter having a slot extending along substantially most of the catheter length, the slot being sufficiently narrow to inhibit unwanted transverse movement of a wire through the slot while being sufficiently resilient to allow forced transverse movement of a wire through the now expanded slot.

FIG. 8 illustrates another embodiment of the present invention, in a "slotted" delivery catheter. Slotted delivery catheter 300 may be seen to include a distal end 302, a distal end port 304, a distal region 306, a proximal region 308, and a lumen 303. Slotted delivery catheter 300 can include a slot 310 extending over a substantial portion of the length of the catheter, and can have a distal unslotted region 311 which can provide column strength. Slot 310 preferably has a width of at least about 0.001 inch. Slot 310 is preferably dimensioned to significantly inhibit the passage of a guide wire, for example a 0.014 inch outside diameter guide wire, through the slot. Slot 310 preferably has a widened distal region or sidewall port 312 dimensioned to freely admit passage of a guide wire therethrough. In some embodiments, distal sidewall port 312 is dimensioned to be about two thousandths of an inch larger than the outside diameter of the guide wire to be used in conjunction with the delivery catheter, or, in the example given, 0.016 inches in width. Port 312 can be skived to provide a shallow entry angle, as previously discussed with respect to other ports. Slot 310 continues to a slot proximal end 316. In a preferred embodiment, slot 310 extends to a proximal end port 318 which is longitudinally accessible from the proximal end of the catheter. Proximal region 308 can include an offset handle 312, shown schematically in FIG. 8. Proximal end port 318 is large enough to admit the wire or shaft of a distal embolic protection device therethrough.

Delivery catheter 300 preferably has a tube wall 322 sufficiently stiff to inhibit the unwanted transverse or radial movement of a wire or shaft through the slot, yet sufficiently resilient to allow a wire or shaft to be forced through the slot, upon the application of sufficient force or pressure, as would not be encountered in use within the human body. Delivery catheter 300 can be formed of polymers well known to those skilled in the art, for example, PEBAX, nylon, PET, Polyimide or HDPE. Slot 310 is preferably between about 0.001 and 0.032 inches in width, more preferably between about 0.001 and 0.010 inches in width. In various embodiments, slot 310 is about 0.001, 0.005, 0.007, 0.009 and 0.010 inches in width and distal sidewall port 312 is at least about 0.016 inches in width. For peripheral applications where 0.035 inch guide wires are commonly used, slot dimensions can be adjusted accordingly. Slot 310 may be seen to terminate distally at distal sidewall port 312. In one embodiment, unslotted portion 311 between slot sidewall port 312 and catheter distal end 302 is between about 5 and 30 centimeters, preferably being at least about 5 centimeters, more preferably being at least about 2 centimeters in length.

Figure 9:
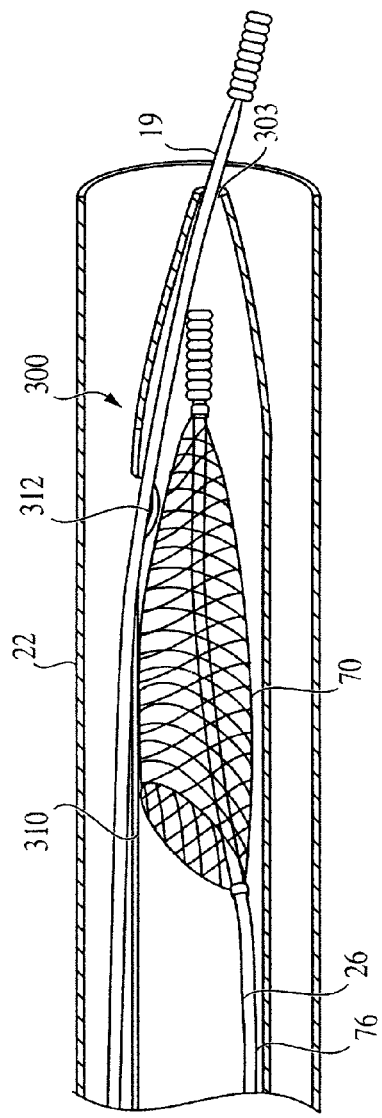
FIG. 9 is a side view of the catheter of FIG. 8, carrying a distal embolic protection device, and being advanced within a guide catheter and over a guide wire.

FIG. 9 illustrates delivery catheter 300, in use within guide catheter 22, disposed over guide wire 19, and carrying distal embolic protection device 26 within. As can be seen from inspection of FIG. 9, guide wire 19 lies within lumen 303 of delivery catheter 300 and extends proximally through lumen 303, exiting delivery catheter 300 through distal sidewall port 312. Distal embolic protection device shaft or wire 76 may be seen to lie within lumen 303. Guide wire 19, delivery catheter 300, and distal embolic protection device 26 can be advanced to a target site, substantially as previously described with respect to other embodiments. Guide wire 19 can extend proximally outside of delivery catheter 300, exiting proximally near the point of entry into the patient.

Figure 10:
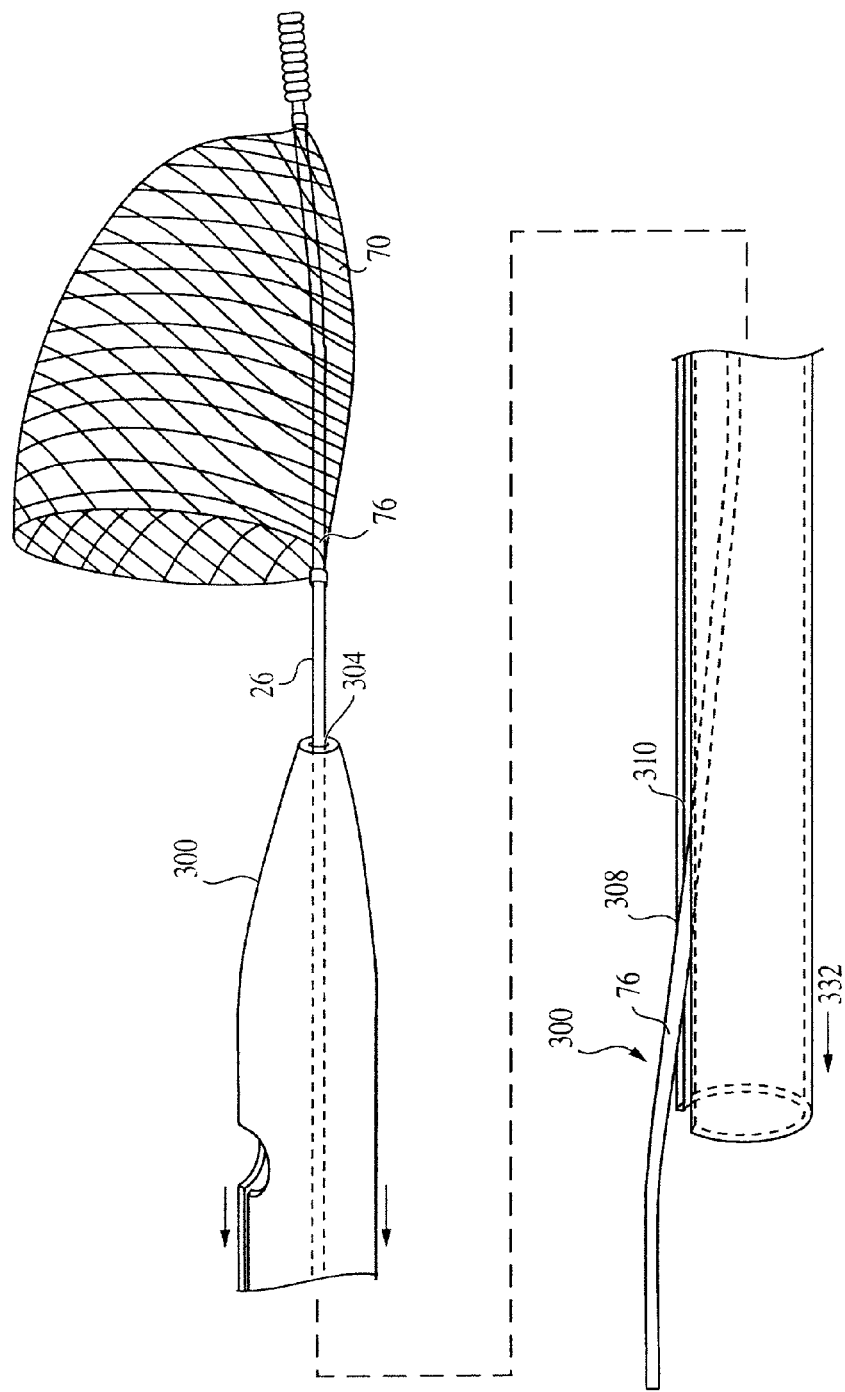
FIG. 10 is a fragmentary, side view of the catheter of FIG. 9, being advanced distally from the guide catheter, having the guide wire proximally withdrawn, and the catheter proximally withdrawn from the deployed distal embolic protection device filter by forcing the distal embolic protection device wire or shaft through the slot.

FIG. 10 illustrates distal embolic protection device 26, having distal embolic protection device distal filter 70 being held in position while delivery catheter 300 is proximally retracted, thereby forcing filter 70 from catheter distal end port 304. Guide wire 19 had previously been proximally withdrawn through distal sidewall port 312, as previously described with respect to other embodiments. FIG. 10 further illustrates slot 310 in proximal region 308, having guide wire 19 being forced transversely through slot 310, thereby forcibly widening the slot width to allow exit of wire 76 through slot 310. The proximal end of distal embolic protection device shaft or wire 76 can be held as indicated at 330 by the treating physician while proximally retracting the delivery catheter as indicated at 332. This can continue as the distal embolic protection device shaft or wire is maintained in a substantially constant position while removing the slotted delivery catheter over the constant position distal embolic protection device shaft or wire 76. In one method, delivery catheter 300 is proximally retracted until the shaft or wire 76 reaches distal sidewall port 312. At this point, the delivery catheter can be further proximally retracted to expose the distal embolic protection device shaft distally extending from distal end port 304 of catheter 300. The exposed shaft 76 can be grasped, and the delivery catheter fully retracted from over the end of the distal embolic protection device shaft or wire 76. The added length to the distal embolic protection device shaft or wire required to allow removal of the delivery catheter over the shaft may be seen to be only the distance between the distal end port 304 and distal sidewall port 312, rather than double the length of the shaft.

The foregoing detailed description should be read with reference to the drawings, in which like elements in different drawings are numbered identically. The drawings, which are not necessarily to scale, depict selected embodiments and are not intended to limit the scope of the invention. Several forms of invention have been shown and described, and other forms will now be apparent to those skilled in art. It will be understood that embodiments shown in drawings and described above are merely for illustrative purposes, and are not intended to limit scope of the invention as defined in the claims which follow.

What is claimed is:

1. A sheath for use during a medical procedure, comprising:
    a tubular member defining a longitudinal axis, and having a proximal end, a proximal end port longitudinally accessible from the proximal end of the tubular member, a distal end, and an outer wall defining a lumen extending through the tubular member, the lumen being in communication with an opening at the distal end of the tubular member, the outer wall including a side port extending radially therethrough with respect to the longitudinal axis, the side port being spaced proximally from the opening at the distal end of the tubular member, the side port defining a point at which the lumen opens to an environment surrounding the sheath;
    a guidewire configured for passage through the opening at the distal end of the tubular member, through the lumen of the tubular member, and through the side port, wherein the outer wall of the tubular member includes a slot formed therein, the slot being in communication with the side port, and extending proximally therefrom, the slot extending to the proximal end port of the tubular member;
    an elongate member at least partially disposed in the lumen of the tubular member; and
    an embolic protection device supported on a distal portion of the elongate member.

2. The sheath of claim 1, wherein the sheath is a rapid exchange sheath.

3. The sheath of claim 1, wherein the distal end of the tubular member is configured for releasable connection to the medical device.

4. The sheath of claim 3, wherein the elongate member and the medical device are positioned within the lumen of the tubular member.

5. The sheath of claim 1, wherein the side port is spaced proximally from the distal end of the tubular member by a distance of 10 centimeters or less.

\* \* \* \* \*